United States Patent
Herman et al.

(10) Patent No.: US 10,417,911 B2
(45) Date of Patent: Sep. 17, 2019

(54) INTER-VEHICLE COOPERATION FOR PHYSICAL EXTERIOR DAMAGE DETECTION

(71) Applicant: Ford Global Technologies, LLC, Dearborn, MI (US)

(72) Inventors: David Michael Herman, Southfield, MI (US); David A. Herman, Southfield, MI (US); Nunzio DeCia, Northville, MI (US); Stephen Jay Orris, Jr., New Boston, MI (US); Nicholas Alexander Scheufler, Flat Rock, MI (US); David Joseph Orris, Southgate, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 19 days.

(21) Appl. No.: 15/846,148

(22) Filed: Dec. 18, 2017

(65) Prior Publication Data
US 2019/0189007 A1    Jun. 20, 2019

(51) Int. Cl.
*G08G 1/017* (2006.01)
*G08G 1/0967* (2006.01)
*G08G 1/16* (2006.01)

(52) U.S. Cl.
CPC ..... *G08G 1/096791* (2013.01); *G08G 1/0175* (2013.01); *G08G 1/096758* (2013.01);
(Continued)

(58) Field of Classification Search
CPC ....... G08G 1/096791; G08G 1/096758; G08G 1/166; G08G 1/161; G08G 1/0175; G08G 1/096775
See application file for complete search history.

(56) References Cited

U.S. PATENT DOCUMENTS

| 5,617,490 A | 4/1997 | Kume |
| 5,717,390 A | 2/1998 | Hasselbring |

(Continued)

FOREIGN PATENT DOCUMENTS

| CN | 106683139 A | 5/2017 |
| CN | 107226087 A | 10/2017 |

(Continued)

OTHER PUBLICATIONS

Besl, Paul J., et al., *A Method for Registration of 3-D Shapes*, IEEE Trans. on Pattern Analysis and Machine Intelligence, 1992, 14 (2): 239-256, IEEE Computer Society: Los Alamitos, CA, USA, 18 pages.

(Continued)

*Primary Examiner* — Joseph Suh
(74) *Attorney, Agent, or Firm* — Frank Lollo; Neal, Gerber & Eisenberg LLP; James P. Muraff (57) ABSTRACT

Method and apparatus herein are for inter-vehicle cooperation for physical exterior damage detection. An example vehicle includes an inter-vehicle communication module and a body control module. The body control module is to monitors an area around the vehicle and characteristics of the vehicle to detect a triggering event and, in response to detecting the trigger event, broadcasts a request for images. Additionally, the body control module generates a composite image based on the images and compares the composite image to a reference image to identify damage on the vehicle. In response to identifying damage, the body control module takes an action specified by an operator.

16 Claims, 3 Drawing Sheets

(52) U.S. Cl.
CPC ....... *G08G 1/096775* (2013.01); *G08G 1/161* (2013.01); *G08G 1/166* (2013.01)

(56) References Cited

U.S. PATENT DOCUMENTS

| | | | |
|---|---|---|---|
| 6,587,597 | B1 | 7/2003 | Nakao |
| 7,586,489 | B2 | 9/2009 | Muller-Fischer |
| 8,228,380 | B2* | 7/2012 | Hardee ................ G08G 1/0175 348/143 |
| 8,473,196 | B2 | 6/2013 | Basnayake |
| 8,817,101 | B2 | 8/2014 | Hanisch |
| 9,135,754 | B2 | 9/2015 | Ng-Thow-Hing |
| 9,165,219 | B2 | 10/2015 | Chen |
| 9,311,818 | B2* | 4/2016 | Lin ........................ G08G 1/166 |
| 9,324,201 | B2* | 4/2016 | Jun ....................... G07C 5/0866 |
| 9,424,725 | B1* | 8/2016 | Keohane ................ G06F 16/29 |
| 9,440,627 | B2 | 9/2016 | Kurtovic et al. |
| 9,477,894 | B1 | 10/2016 | Reed et al. |
| 9,547,912 | B2 | 1/2017 | Kotz et al. |
| 9,558,667 | B2 | 1/2017 | Bowers |
| 9,672,440 | B2* | 6/2017 | Saward ................. H04N 7/181 |
| 9,762,880 | B2 | 9/2017 | Pflug |
| 9,784,887 | B1* | 10/2017 | Ulmer ..................... G01W 1/02 |
| 9,813,619 | B2 | 11/2017 | An |
| 9,928,544 | B1 | 3/2018 | Hasan |
| 2002/0130953 | A1 | 9/2002 | Riconda |
| 2003/0212567 | A1* | 11/2003 | Shintani ................ G06Q 99/00 725/105 |
| 2009/0231469 | A1 | 9/2009 | Kato |
| 2011/0218896 | A1* | 9/2011 | Tonnon ................ G06Q 40/123 705/31 |
| 2013/0103305 | A1 | 4/2013 | Becker et al. |
| 2013/0342333 | A1 | 12/2013 | Hutchings |
| 2014/0324247 | A1* | 10/2014 | Jun ....................... G07C 5/0866 701/1 |
| 2015/0054716 | A1* | 2/2015 | Hirabayashi ....... G02B 27/0093 345/8 |
| 2015/0054934 | A1* | 2/2015 | Haley ................ G06K 9/00845 348/78 |
| 2015/0134675 | A1* | 5/2015 | Ellis ...................... G06F 16/335 707/754 |
| 2016/0153778 | A1 | 6/2016 | Singh et al. |
| 2016/0325741 | A1* | 11/2016 | Furst ................... B60R 21/0134 |
| 2016/0371968 | A1* | 12/2016 | Almansour ............ G06Q 10/00 |
| 2017/0011378 | A1* | 1/2017 | Inoue .................... G06T 15/205 |
| 2017/0195564 | A1 | 7/2017 | Appia |
| 2017/0261336 | A1* | 9/2017 | Schmidt ................ G01C 21/165 |
| 2017/0300761 | A1 | 10/2017 | Chaney, Jr. et al. |
| 2017/0374502 | A1* | 12/2017 | Gabel ...................... H04W 4/02 |
| 2018/0001814 | A1* | 1/2018 | Salter ..................... B60Q 1/085 |
| 2018/0027224 | A1* | 1/2018 | Javidnia ............... H04N 13/239 382/154 |
| 2018/0032829 | A1* | 2/2018 | Kim ....................... G06Q 50/10 |
| 2018/0219643 | A1 | 8/2018 | Naka |
| 2018/0290594 | A1* | 10/2018 | Abdel-Rahman ......... B60R 1/06 |
| 2018/0321905 | A1* | 11/2018 | Fountaine ............... G06F 3/167 |

FOREIGN PATENT DOCUMENTS

| | | |
|---|---|---|
| DE | 102009031319 A1 | 1/2011 |
| DE | 102016212181 A1 | 1/2018 |
| EP | 1462762 A1 | 9/2004 |
| JP | 2017068640 A | 4/1917 |
| JP | 2005005978 A | 1/2005 |
| JP | 2005209079 A | 8/2005 |
| KR | 101760312 B1 | 7/1917 |

OTHER PUBLICATIONS

Brailean, James C., et al., *Noise Reduction filters for dynamic image sequences: A review*, Proceedings of the IEEE, 1995, 83.9: 1272-1292, 21 pages.

Buades, Antoni, et al., *Multi image noise estimation and denoising*, 2010, 29 pages.

Carceroni, Rodrigo, et al., *Structure from motion with known camera positions*, Computer Vision and Pattern Recognition, 2006, IEEE Computer Society Conference on vol. 1, 10 pages.

Chen, H., et al., *3D free-form object recognition in range images using local surface patches*, 2007, Pattern Recognition Letters, vol. 28, No. 10. 4 pages.

Chwa, Dongkyoung, et al., *Camera motion estimation for 3-D structure reconstruction of moving objects*, 2012 IEEE International Conference on Systems, Man, and Cybernetics (SMC), 6 pages.

Crandall, David J., et al. *SfM with MRFs: Discrete-Continuous Optimization for Large-Scale Structure from Motion*, IEEE Transactions on Pattern Analysis & Machine Intelligence, 2013, vol. 35, No. 12, 14 pages.

Dekeyser, Fabien, et al. *Restoration of noisy, blurred, undersampled image sequences using a parametric motion model*, 2000, Proc. of the ISIVC, 14 pages.

Dubois, Eric et al., *Noise reduction in image sequences using motion-compensated temporal filtering*, 1984, IEEE transactions on communications 32.7, 7 pages.

Nilosek, David et al., *Assessing geoaccuracy of structure from motion point clouds from long-range image collections*, Optical Engineering, 2014, 53.11, 11 pages.

Papazov, Chavdar, et al., *An efficient ransac for 3d object recognition in noisy and occluded scenes*, Asian Conference on Computer Vision, 2010, Springer, Berlin, Heidelberg, 14 pages.

Rosman, Guy, et al., *Patch-Collaborative Spectral Point-Cloud Denoising*, Computer Graphics Forum, 2013, vol. 32, No. 8, 12 pages.

Tombari, F., et al. *Object recognition in 3D scenes with occlusions and clutter by Hough voting*, 2010, 4th Pacific-Rim Symposium on Image and Video Technology, 7 pages.

Badrinarayanan, Vijay et al., SegNet: A Deep Convolutional Encoder-Decoder Architecture for Image Segmentation, Oct. 2016, 14 pages.

Brostow, Gabriel J., Segmentation and Recognition using Structure from Motion Point Clouds, 2008, 14 pages.

Chen, Liang-Chi Eh et al., DeepLab: Semantic Image Segmentation with Deep Convolutional Nets, Atrous Convolution, and Fully Connected CRFs, May 2017, 14 pages.

Eigen, David et al., Depth Map Prediction From a Single Image Using a Multi-Scale Deep Network, 2014, 9 pages.

Finlayson, Graham, Detecting Illumination in Images, 2007, 8 pages.

Girdhar, Rohit et al., Learning a Predictable and Generative Vector Representation for Objects, Springer International Publishing, 2016, 26 pages.

Hui, Tak-Wai et al., Depth Map Super-Resolution by Deep Multi-Scale Guidance, Springer International Publishing, 2016, 17 pages.

Izadi, Shahram, KinectFusion: Real-Time 3D Reconstruction and Interaction Using a Moving Depth Camera, 2011, 10 pages.

Laskowski, Maciej, Detection of Light Sources in Digital Photographs, 2007, 6 pages.

Lin, Guosheng et al., RefineNet: Multi-Path Refinement Networks for High-Resolution Semantic Segmentation, Nov. 2016, 11 pages.

Lin, Shu-Chin et al., Filling Holes in 3D Scanned Model Base on 2D Image Inpainting, 2017, 6 pages.

Long, Jonathan et al., Fully Convolutional Networks for Semantic Segmentation, Mar. 2015, 10 pages.

Marton, Zoltan Csaba, On Fast Surface Reconstruction Methods for Large and Noisy Point Clouds, 2009, 6 pages.

Nguyen, Anh, 3D Point Cloud Segmentation: A Survey, 2013, 6 pages.

Pauly, Mark, Efficient Simplification of Point-Sampled Surfaces, 2002, 8 pages.

Peng Chao et al., Large Kernel Matters—Improve Semantic Segmentation by Global Convolutional Network, Mar. 2017, 11 pages.

Remondino, Fabio, From Point Cloud to Surface: The Modeling and Visualization Problem, 2003, 11 pages.

Xiang, Yu et al., ObjectNet3D: A Large Scale Database for 3D Object Recognition, 2016, 16 pages.

Yu, Fisher et al., Multi-Scale Context Aggregation by Dilated Convolutions, Apr. 2016, 13 pages.

(56) References Cited

OTHER PUBLICATIONS

Zach, Christopher, Fast and High Quality Fusion of Depth Maps, 2008, 8 pages.
Zhang, Yiwei et al., A Fast 3D Reconstruction System With a Low-Cost Camera Accessory, 2015, 7 pages.
Zhao, Hengshuang et al., Pyramid Scene Parsing Network, Apr. 2017, 11 pages.
Zhu, Zhuotun et al., Deep Learning Representation using Autoencoder for 3D Shape Retrieval, 2016, 6 pages.
Mitra, Niloy J. et al., "*Estimating Surface Normals in Noisy Point Cloud Data*," International Journal of Computational Geometry & Applications, pp. 261-276, vol. 14, 2004, 16 pages.
Han, Xian-Feng et al., "*A Review of Algorithms for Filtering the 3D Point Cloud*," Signal Processing: Image Communication, pp. 103-112 2017, 10 pages.

* cited by examiner

INTER-VEHICLE COOPERATION FOR PHYSICAL EXTERIOR DAMAGE DETECTION

TECHNICAL FIELD

The present disclosure generally relates to vehicle-to-vehicle communication and, more specifically, inter-vehicle cooperation for physical exterior damage detection.

BACKGROUND

Vehicles, especially those that park and operate in an urban environment, are subject to events that cause damage to the exterior of the vehicle during periods where, for example, the vehicle is infrequently driven (e.g., the owner commutes using public transportation and drives on the weekends, etc.). Additionally, companies operate fleets of vehicles where manual inspection for exterior damage may be time-consuming. The fleet monitoring issue is magnified when the vehicles are autonomous so there are no drivers to inspect the vehicles before or after operation.

SUMMARY

The appended claims define this application. The present disclosure summarizes aspects of the embodiments and should not be used to limit the claims. Other implementations are contemplated in accordance with the techniques described herein, as will be apparent to one having ordinary skill in the art upon examination of the following drawings and detailed description, and these implementations are intended to be within the scope of this application.

Example embodiments are disclosed for inter-vehicle cooperation for physical exterior damage detection. An example vehicle includes an inter-vehicle communication module and a body control module. The body control module is to monitors an area around the vehicle and characteristics of the vehicle to detect a triggering event and, in response to detecting the trigger event, broadcasts a request for images. Additionally, the body control module generates a composite image based on the images and compares the composite image to a reference image to identify damage on the vehicle. In response to identifying damage, the body control module takes an action specified by an operator.

An example method to detect damage of a vehicle includes monitoring, with trigger sensors, an area around the vehicle and characteristics of the vehicle to detect a triggering event. The method also includes in response to detecting the trigger event, broadcast, via an inter-vehicle communication module, a request for images, and generating a composite image based on the images. Additionally, the method includes comparing the composite image to a reference image to identify damage on the vehicle and, in response to identifying damage, take an action specified by an operator.

BRIEF DESCRIPTION OF THE DRAWINGS

For a better understanding of the invention, reference may be made to embodiments shown in the following drawings. The components in the drawings are not necessarily to scale and related elements may be omitted, or in some instances proportions may have been exaggerated, so as to emphasize and clearly illustrate the novel features described herein. In addition, system components can be variously arranged, as known in the art. Further, in the drawings, like reference numerals designate corresponding parts throughout the several views.

DETAILED DESCRIPTION OF EXAMPLE EMBODIMENTS

While the invention may be embodied in various forms, there are shown in the drawings, and will hereinafter be described, some exemplary and non-limiting embodiments, with the understanding that the present disclosure is to be considered an exemplification of the invention and is not intended to limit the invention to the specific embodiments illustrated.

Timely detection of exterior physical damage, such as scratches, dents, and graffiti, etc., helps maintain a vehicle and determine fault in the case of an accident or malicious act. As used herein, the term "damage" refers to physical, aesthetic, and other modifications that effect the operation of the vehicle. For example, when an autonomous vehicle traversing a higher crime region and an individual approaches the car in traffic and remains stationary while the car is stopped at a light, it is desirable to determine whether the individual caused damage (such as graffiti) to the unoccupied vehicle. Detecting damage facilitates the vehicle taking steps to ameliorate the damage. For example, an autonomous vehicle may, upon detecting exterior damage, notify the owner and navigate itself to a repair facility.

As described below, a vehicle autonomously detects exterior physical damage by (a) in response to a triggering event, requesting, via inter-vehicle communication, images and/or other imaging data (e.g., topographic data from LiDAR, etc.) from nearby vehicle and/or infrastructure nodes, (b) creating a model of the vehicle using a Structure from Motion based on the received images, and (c) compares the constructed model to a reference model to identify the location, type, and/or severity of exterior damage. Additionally, in some examples, when the vehicle is in motion, the received images are segmented to remove the varying backgrounds to obtain to increase the accuracy of the structure-from-motion technique. When the exterior damage is detected, the vehicle performs one or more actions. For example, the vehicle may notify authorities, notify an insurance company, notify the owner of the vehicle, inform a mobile repair team, and/or autonomously navigate to a maintenance facility, etc.

Before a vehicle leaves the factory, the exterior of the vehicle is photographed from multiple orientations, rotations, and/or heights. Additionally, in some example, a 3D model of the vehicle is creates. The images and/or models are combined to create a reference to compare to later constructed vehicle models to detect changes in color, shape, and/or paint integrity. For example, the reference model may be used to determine that one or more hubcaps of the vehicle have been stolen. The vehicle includes an inter-vehicle communication module (IVCM) that communicates with other vehicles and/or infrastructure based nodes (sometimes referred to as "roadside units"). The inter-vehicle communication module include hardware and software to implement a vehicle-to-vehicle communication protocol, such as Dedicated Short Range Communication (DSRC). Upon detection of a triggering event, the vehicle broadcasts a request for other vehicles and infrastructure based nodes in the area that are equipped with a camera to, if possible, take images of the vehicle and send those image to the vehicle. The triggering event is when the vehicle determines a likelihood that damage has occurred. For example, based on the location, the vehicle may trigger damage detection when an individual is detected proximate the vehicle for an extended period of time while the vehicle is stationary. As another example, the vehicle may trigger damage detection when the vehicle has been stationary in a location for an extended period of time, such as two or three days. When damage is detected, the vehicle performs actions to assist the owner to ameliorate the damage. For example, the vehicle may (a) contact the police, (b) generate a report and submit it to the police, (c) generate a report and submit it as an insurance claim, (d) request a quote from a repair shop and/or schedule an appointment, and/or (e) notify the owner, etc.

Figure 1:
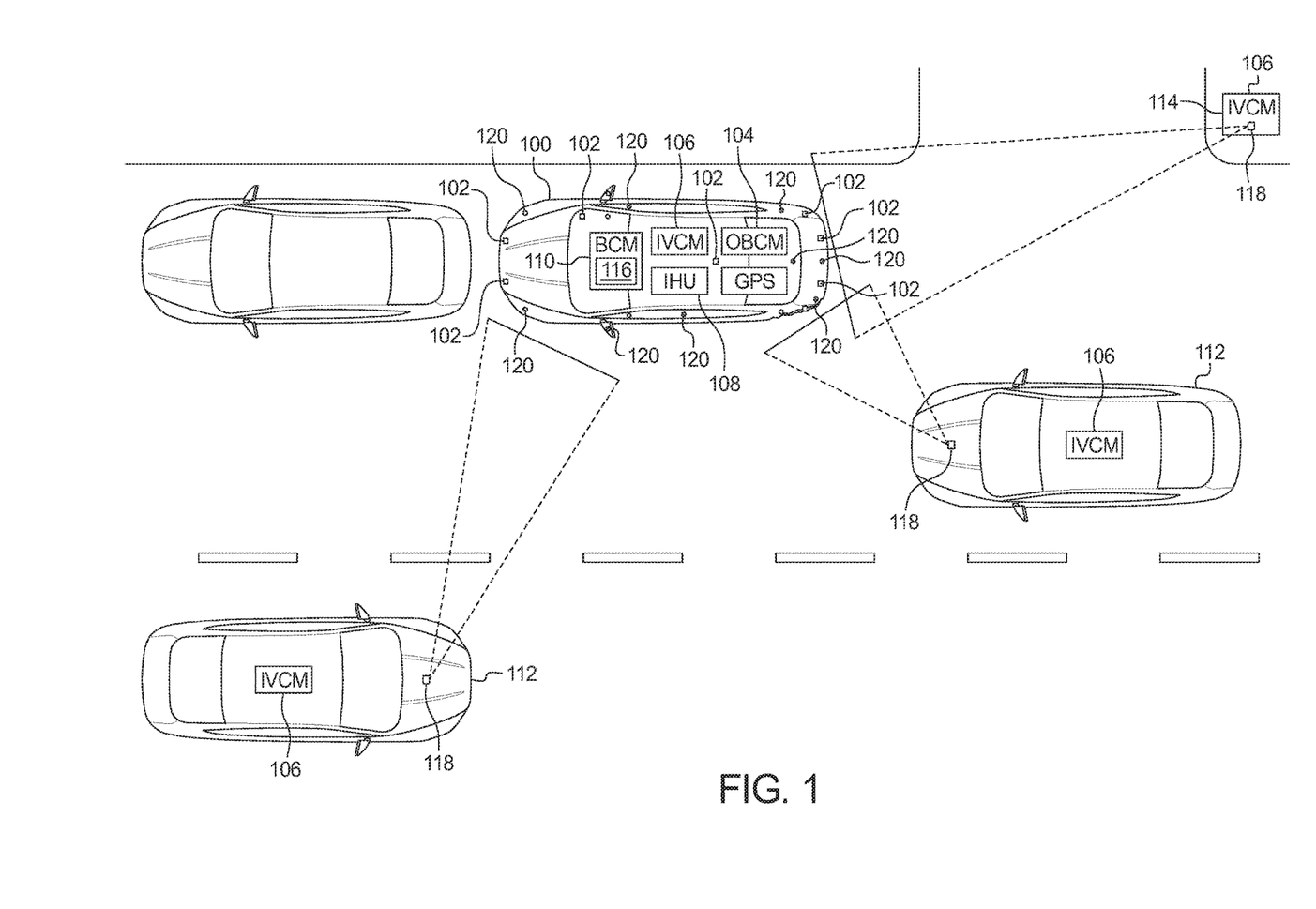
FIG. 1 illustrates a vehicle operating in accordance with the teachings of this disclosure.

FIG. 1 illustrates a vehicle 100 operating in accordance with the teachings of this disclosure. The vehicle 100 may be a standard gasoline powered vehicle, a hybrid vehicle, an electric vehicle, a fuel cell vehicle, and/or any other mobility implement type of vehicle. The vehicle 100 includes parts related to mobility, such as a powertrain with an engine, a transmission, a suspension, a driveshaft, and/or wheels, etc. The vehicle 100 may be non-autonomous, semi-autonomous (e.g., some routine motive functions controlled by the vehicle 100), or autonomous (e.g., motive functions are controlled by the vehicle 100 without direct driver input). In the illustrated example the vehicle 100 includes triggering sensors 102, an on-board communication module (OBCM) 104, an inter-vehicle communication module (IVCM) 106, an infotainment head unit (IHU) 108, and a body control module 110.

The triggering sensors 102 are sensors that monitor the area around the vehicle 100 to detect events that are indicative to potential damage to the vehicle 100. In some examples, the triggering sensors 102 include cameras, range detection sensors (e.g., radar, LiDAR, ultrasonic, infrared, etc.), accelerometers, axial sensors (e.g., yaw and pitch sensors, etc.), microphones, scratch detection sensors, etc. An example scratch detection sensor is described in U.S. patent application Ser. No. 15/427,779 entitled, "Vehicle Scratch Detection and Monitoring," which is incorporated by reference herein in its entirety. The triggering sensors 102 are used to (a) detect suspicious activity by tracking individuals in the vicinity of the vehicle 100, (b) detect physical indicia of impacts, and/or (c) auditory indicia of impacts and other damage. For example, the accelerometers and axial sensors may be used to detect when another vehicle impacts the host vehicle 100. As another example, the microphones and/or the cameras may be used to detect when a rock hits the front windshield of the vehicle 100.

The on-board communications module 104 includes wired or wireless network interfaces to enable communication with external networks. The on-board communications module 104 includes hardware (e.g., processors, memory, storage, antenna, etc.) and software to control the wired or wireless network interfaces. In the illustrated example, the on-board communications module 104 includes one or more communication controllers for standards-based networks (e.g., Global System for Mobile Communications (GSM), Universal Mobile Telecommunications System (UMTS), Long Term Evolution (LTE), Code Division Multiple Access (CDMA), WiMAX (IEEE 802.16m); local area wireless network (including IEEE 802.11 a/b/g/n/ac or others), and Wireless Gigabit (IEEE 802.11ad), etc.). In some examples, the on-board communications module 104 includes a wired or wireless interface (e.g., an auxiliary port, a Universal Serial Bus (USB) port, a Bluetooth® wireless node, etc.) to communicatively couple with a mobile device (e.g., a smart phone, a smart watch, a tablet, etc.). In such examples, the vehicle 100 may communicated with the external network via the coupled mobile device. The external network(s) may be a public network, such as the Internet; a private network, such as an intranet; or combinations thereof, and may utilize a variety of networking protocols now available or later developed including, but not limited to, TCP/IP-based networking protocols.

The inter-vehicle communication module 106 includes antenna(s), radio(s) and software to broadcast messages and to establish communication between the host vehicle 100 and other vehicle 112, infrastructure-based modules 114, and mobile device-based modules (not shown). More information on the inter-vehicle communication network and how the network may communicate with vehicle hardware and software is available in the U.S. Department of Transportation's Core June 2011 System Requirements Specification (SyRS) report (available at www.its.dot.gov/meetings/pdf/CoreSystem_SE_SyRS_RevA %20(2011-06-13).pdf), which is hereby incorporated by reference in its entirety along with all of the documents referenced on pages 11 to 14 of the SyRS report. The inter-vehicle communication systems may be installed on vehicles and along roadsides on infrastructure. The inter-vehicle communication systems incorporated into infrastructure (e.g., traffic signals, street lights, municipal cameras, etc.) is known as a "roadside" system or unit. inter-vehicle communication may be combined with other technologies, such as Global Position System (GPS), Visual Light Communications (VLC), Cellular Communications, and short range radar, facilitating the vehicles communicating their position, speed, heading, relative position to other objects and to exchange information with other vehicles or external computer systems. inter-vehicle communication systems can be integrated with other systems such as mobile phones.

In some examples, the inter-vehicle communication module 106 implements the Dedicated Short Range Communication (DSRC) protocol. Currently, the DSRC network is identified under the DSRC abbreviation or name. However, other names are sometimes used, usually related to a Connected Vehicle program or the like. Most of these systems are either pure DSRC or a variation of the IEEE 802.11 wireless standard. However, besides the pure DSRC system it is also meant to cover dedicated wireless communication systems between cars and roadside infrastructure system, which are integrated with GPS and are based on an IEEE 802.11 protocol for wireless local area networks (such as, 802.11p, etc.).

The infotainment head unit 108 provides an interface between the vehicle 100 and a user. The infotainment head unit 108 includes digital and/or analog interfaces (e.g., input devices and output devices) to receive input from the user(s) and display information. The input devices may include, for example, a control knob, an instrument panel, a digital camera for image capture and/or visual command recognition, a touch screen, an audio input device (e.g., cabin microphone), buttons, or a touchpad. The output devices may include instrument cluster outputs (e.g., dials, lighting devices), actuators, a heads-up display, a center console display (e.g., a liquid crystal display ("LCD"), an organic light emitting diode ("OLED") display, a flat panel display, a solid state display, etc.), and/or speakers. In the illustrated example, the infotainment head unit 108 includes hardware (e.g., a processor or controller, memory, storage, etc.) and software (e.g., an operating system, etc.) for an infotainment system (such as SYNC® and MyFord Touch® by Ford®, Entune® by Toyota®, IntelliLink® by GMC®, etc.). Additionally, the infotainment head unit 108 displays the infotainment system on, for example, the center console display. The infotainment head unit 108 facilitates the user entering in preferences (e.g., how often to trigger the damage detection when the vehicle is stationary, etc.) and information (e.g., the contact information for insurance and/or a repair shop, etc.). The infotainment head unit 108 also facilitates the user viewing the reconstructed images and the vehicle 100 and/or progress of reconstructing the image of the vehicle 100.

The body control module 110 controls various subsystems of the vehicle 100. For example, the body control module 110 may control power windows, power locks, an immobilizer system, and/or power mirrors, etc. The body control module 110 includes circuits to, for example, drive relays (e.g., to control wiper fluid, etc.), drive brushed direct current (DC) motors (e.g., to control power seats, power locks, power windows, wipers, etc.), drive stepper motors, and/or drive LEDs, etc. In the illustrated example, the body control module 110 includes a damage detector 116. Alternatively, in some examples, the damage detector 116 may incorporated into another vehicle module, such as the infotainment head unit 108.

The damage detector 116 determines when the vehicle 100 is damaged. For example, the damage detector 116 may detect cosmetic damage (e.g., from graffiti, scratched paint, etc.), structural damage (e.g., dents, etc.), and/or missing components (e.g., such as hub caps, tires, etc.). To detect damage, the damage detector 116 (a) monitors the area around the vehicle 100 and the structural integrity of the vehicle 100 to detect a triggering event, (b) determine attributes of the vehicle 100 (e.g., vehicle location, speed, brake status, etc.) (c) requests images from other vehicles 112 and roadside units 114 that are equipped with cameras 118 to capture and send images to the vehicle 100, (d) create an composite image using the received image using a Structure-of-Motion technique, (e) compare the composite image to reference images to detect damage to the vehicle 100, and (f) take actions to help the user ameliorate the damage. The Structure-of-Motion technique produces a three-dimensional (3D) point cloud that is used to match a with 3D model of the vehicle 100 to detect damage and visually inspect the vehicle 100.

When the vehicle 100 is manufactured or from time-to-time (e.g., after a major repair, etc.), the exterior of the vehicle 100 is imaged from multiple orientations, rotations, and heights around the vehicle 100 to generate a set of reference images. Additionally, a model is generated based on the exterior dimensions of the vehicle 100. Alternatively, in some example, the reference images are generated on the basis of make/model/color variant (e.g., each vehicle 100 of a certain make, model, and color will have a corresponding generic set of reference images). The set of reference images are stored in memory (e.g., the memory 206 of FIG. 2 below) of the vehicle 100 and are used by the damage detector 116 to detect changes in the exterior of the vehicle 100 indicative of damage.

To detect trigger events, the damage detector 116 (a) monitors the environment around the vehicle 100 and the characteristics of the vehicle 100 (e.g., with the triggering sensors 102) and/or (b) tracks time or distance based milestones. In some examples, the trigger events include the damage detector 116 detecting a possible impact to the vehicle 100 based on range detection sensor readings. In some such examples, the triggering event is based on a probability of an impact taking into account the error in the range detection sensor measurements. For example, if one of the range detection sensors has a known accuracy of ±3.5 centimeters (cm) and the range detection sensor detects another object within 3 cm of the vehicle 100, the damage detector 116 may determine that there has been a trigger event. In some examples, the trigger events include detecting an impact on the vehicle 100 with the triggering sensors 102. For example, an acceleration pattern may be indicative of another object (such as a vehicle or a shopping cart, etc.) colliding with the vehicle 100. In some examples, the triggering event include detecting a noise indicative of a damaging event, such as a collision, and/or a rock hitting the windshield, etc. In some examples, the trigger events include the damage detector 116 detecting that a person is next to the vehicle 100 for a threshold period of time while the vehicle is stationary. In some such examples, the damage detector 116 performs image analysis to determine whether the person is holding something (such as a spray paint can or a knife, etc.). For example, a person with an object in their hand that stands next to the vehicle for an extended period of time may be applying graffiti to the vehicle 100. In some examples, the trigger events include detecting that one of the sensors of the vehicle 100 (e.g., one of the triggering sensors 102, etc.) is failing or degrading (e.g., as determined by the diagnostics of the sensor) for a threshold period of time.

In some examples, the trigger events include time or mileage thresholds. In some examples, the threshold are adjustable by the operator (e.g., via the infotainment head unit 108. For example, the damage detector 116 may detect a trigger event every 1,000 miles of travel above 15,000 miles of accumulative travel. In some examples, the time or mileage thresholds are based on an OEM predictive maintenance schedule. As another example, the damage detector 116 may detect a trigger event when the vehicle has remained stationary at the same location for more than 2 days. In some examples, the trigger events include location based triggers. For example, the damage detector 116 may detect a triggering event based on (i) the location that the vehicle 100 is parked at and (ii) property damage crime statistics for that location. As another example, the damage detector 116 may detect a trigger event after inclement weather at the location of the vehicle (e.g., after a hail storm, etc.). In some examples, the trigger events include the motive condition of the vehicle 100. For example, the damage detector 116 may detect a trigger event every time the vehicle 100 has been parked for more than 5 minutes. In some examples, the trigger events may be externally triggered. For example, a vendor may set up a roadside unit 114 to broadcast a message to trigger the damage detector 116. In that example, the vendor may be a car wash or a auto body repair shop.

The damage detector 116 records vehicle characteristics when a trigger event is detected. The vehicle characteristics include location (e.g., GPS coordinates), position relative to the roadway, and/or occupancy, etc. The vehicle characteristics are sent as part of the imaging request to facilitate the other vehicles 112 determine the relative location of the host vehicle 100.

In response to detecting a trigger event, the damage detector 116 broadcasts an image request via the inter-vehicle communication module 106. The image request causes other vehicles 112 that have the inter-vehicle communication module 106 to determine the location of the host vehicle 100 relative to the location of the other vehicle 112 in order for the other vehicles 112 to capture images of the host vehicle 100. In some examples, when the vehicle 100 is autonomous, the vehicle 100 determines whether it is in bad positioned to be photographed. For example, the range detection sensors may detect that the vehicle 100 is parked close to adjacent vehicles in a manner so that the vehicle 100 cannot be seen from several angles. In some such examples, the vehicle 100 autonomously repositions and/or adjusts its speed relative to nearby vehicles 112 so that it is in a better location to be photographed. In some such examples, the vehicle repositions itself or alters its course when the damage detector 116 determines that the area around the vehicle 100 is poorly lit. For example, the vehicle 100 may change its route to a street with more street lights. The images sent by the other vehicles 112 include a time stamp, a position, and approximate orientation of the camera in space.

The damage detector 116 analyzes the images received from the other vehicle(s) 112 and/or the roadside unit(s) 114 to generate a composite model of the vehicle and compares the generate composite to the model and set of reference images stored in the memory. The damage detector 116 also determines whether a received image is suitable for determining the condition of the vehicle 100 based on ability to locate the vehicle in the image and/or determining whether the perspective of the image provides information to construct the composite. To detect objects and/or the host vehicle 100 in the received images, the damage detector 116 uses feature detection techniques (e.g., a scale-invariant feature transform (SIFT) technique, a speeded up robust features (SURF) technique, convolution neural network for semantic segmentation or feature detection, etc.). For example, color based detection may be used in color images to distinguish the same car model from another when the paint color differs. The feature detections identifies feature points 120 of the vehicle 100 in the images. The damage detector 116 uses multiple images received from different ones of the other vehicle(s) 112 and/or the roadside unit(s) 114 from different angles, orientations, distances, etc. to reconstruct the 3D scene via a structure from motion algorithm. Using the model of the vehicle 100 store in memory and the known feature points 120 as anchors to related the various images, the damage detector 116 stitches the images together to form the composite model. Examples of the structure from motion algorithm are described in Crandall, David J., et al. "SfM with MRFs: Discrete-continuous optimization for large-scale structure from motion." *IEEE transactions on pattern analysis and machine intelligence* 35.12 (2013): 2841-2853, which is incorporated by reference in its entirety. In some examples, other object around the vehicle 100 are also used as anchor point to relate the received images to the vehicle 100. For example, if the vehicle 100 detects a fire hydrant 2 meters ahead on the right of the vehicle 100 and one of the received images also shows the fire hydrant in view of the vehicle 100, that information may be used to estimate the exterior camera position when the image was captured to improve the accuracy of the structure-from-motion technique.

In some examples, depth information (e.g., from LiDAR and/or radar, etc.) is also requested from the other vehicles 112 and/or the roadside units 114 when the area around the vehicle 100 is crowded with objects and identifying the host vehicle 100 may be difficult. For example, a bumper to bumper traffic may provide multiple vantage points of the vehicle 100. However, in such an example, occlusion of the vehicle 100 may occur from a number of the images. The stitching of the 3D scene may assist in geo-locating the camera of the other vehicle 112 that is the source of the image relative to the vehicle 100.

The damage detector 116 compares the composite image/model to the set of reference images to determine whether the vehicle 100 has been damaged. The detected damage may include graffiti, body damage (e.g., dents, scratches, etc.) and/or missing components (e.g., tires, hubcaps, windows, etc.), etc. In some examples, the damage detector 116 also detects when extra objects are contacting the vehicle 100. For example, an analysis of the image/model may show that a tree branch is on top of the vehicle 100 or a teenager is riding on the vehicle or in the truck bed of the vehicle 100. Depending on the detected damage, the damage detector 116 responding detecting the damage to the vehicle 100. The damage detector 116 (a) contacts the police, (b) generates and sends a report to the polices, (c) generates and sends an insurance claim, (d) contacts a repair shop, (e) makes an appointment at the repair shop, (f) requests onsite service from a repair shop, and/or (g) contacts the operator. In some examples, when generating a report and/or contacting an entity (e.g., the police, the insurance company, the operator, the owner, etc.), the damage detector 116 includes the composite image. In some examples, a profile or the operator and/or owner is stored in memory. The profile includes contact information (e.g., telephone numbers, email addresses, etc.) for the owner/operator, the owner's insurance, and/or a preferred body shop.

Figure 2:
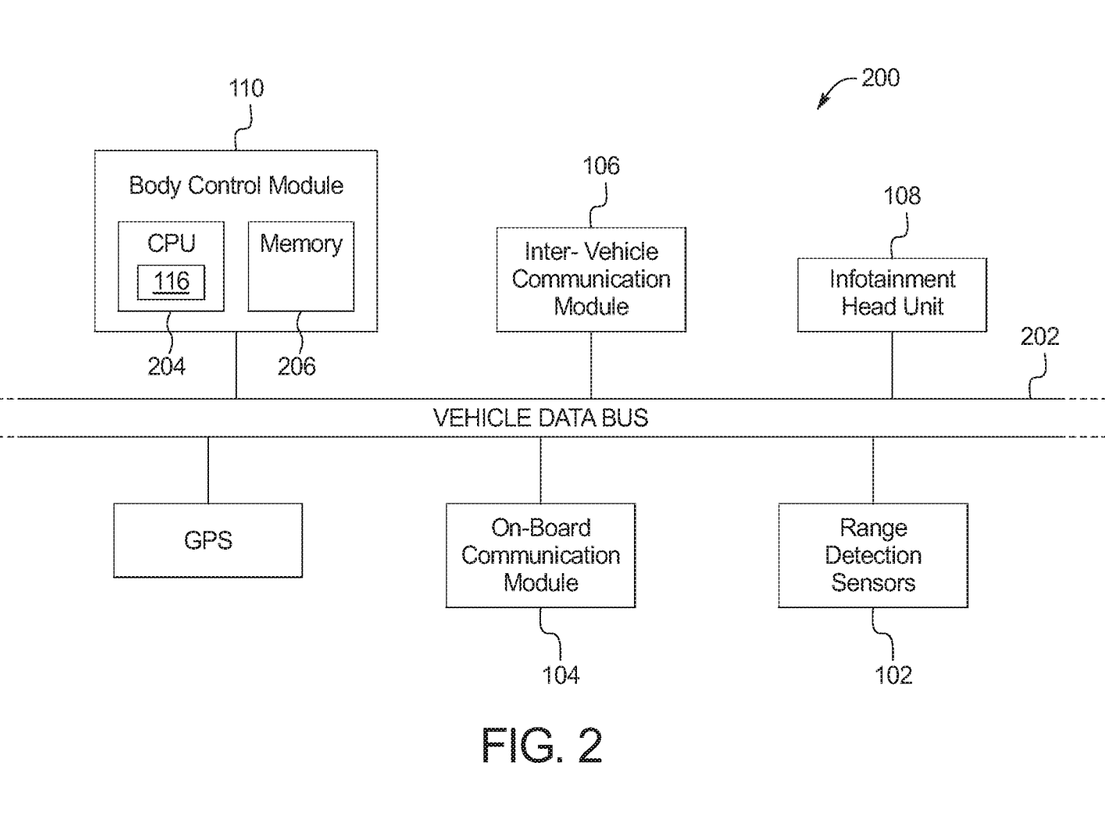
FIG. 2 is a block diagram of electronic components of the vehicle of FIG. 1.

FIG. 2 is a block diagram of electronic components 200 of the vehicle 100 of FIG. 1. In the illustrated example, the electronic components 200 include the triggering sensors 102, the on-board communications module 104, the inter-vehicle communication module 106, the infotainment head unit 108, the body control module 110, and a vehicle data bus 202.

In the illustrated example, the body control module 110 includes a processor or controller 204 and memory 206. In the illustrated example, the body control module 110 is structured to include damage detector 116. Alternatively, in some examples, the damage detector 116 may be incorporated into another electronic control unit (ECU) with its own processor and memory (such as the infotainment head unit 108, etc.). The processor or controller 204 may be any suitable processing device or set of processing devices such as, but not limited to: a microprocessor, a microcontroller-based platform, a suitable integrated circuit, one or more field programmable gate arrays (FPGAs), and/or one or more application-specific integrated circuits (ASICs). The memory 206 may be volatile memory (e.g., RAM, which can include non-volatile RAM, magnetic RAM, ferroelectric RAM, and any other suitable forms); non-volatile memory (e.g., disk memory, FLASH memory, EPROMs, EEPROMs, non-volatile solid-state memory, etc.), unalterable memory (e.g., EPROMs), read-only memory, and/or high-capacity storage devices (e.g., hard drives, solid state drives, etc). In some examples, the memory 206 includes multiple kinds of memory, particularly volatile memory and non-volatile memory.

The memory 206 is computer readable media on which one or more sets of instructions, such as the software for operating the methods of the present disclosure can be embedded. The instructions may embody one or more of the methods or logic as described herein. In a particular embodiment, the instructions may reside completely, or at least partially, within any one or more of the memory 206, the computer readable medium, and/or within the processor 204 during execution of the instructions.

The terms "non-transitory computer-readable medium" and "tangible computer-readable medium" should be understood to include a single medium or multiple media, such as a centralized or distributed database, and/or associated caches and servers that store one or more sets of instructions. The terms "non-transitory computer-readable medium" and "tangible computer-readable medium" also include any tangible medium that is capable of storing, encoding or carrying a set of instructions for execution by a processor or that cause a system to perform any one or more of the methods or operations disclosed herein. As used herein, the term "tangible computer readable medium" is expressly defined to include any type of computer readable storage device and/or storage disk and to exclude propagating signals.

The vehicle data bus 202 communicatively couples the triggering sensors 102, the on-board communications module 104, the inter-vehicle communication module 106, the infotainment head unit 108, and the body control module 110. In some examples, the vehicle data bus 202 includes one or more data buses. The vehicle data bus 202 may be implemented in accordance with a controller area network (CAN) bus protocol as defined by International Standards Organization (ISO) 11898-1, a Media Oriented Systems Transport (MOST) bus protocol, a CAN flexible data (CAN-FD) bus protocol (ISO 11898-7) and/a K-line bus protocol (ISO 9141 and ISO 14230-1), and/or an Ethernet™ bus protocol IEEE 802.3 (2002 onwards), etc.

Figure 3:
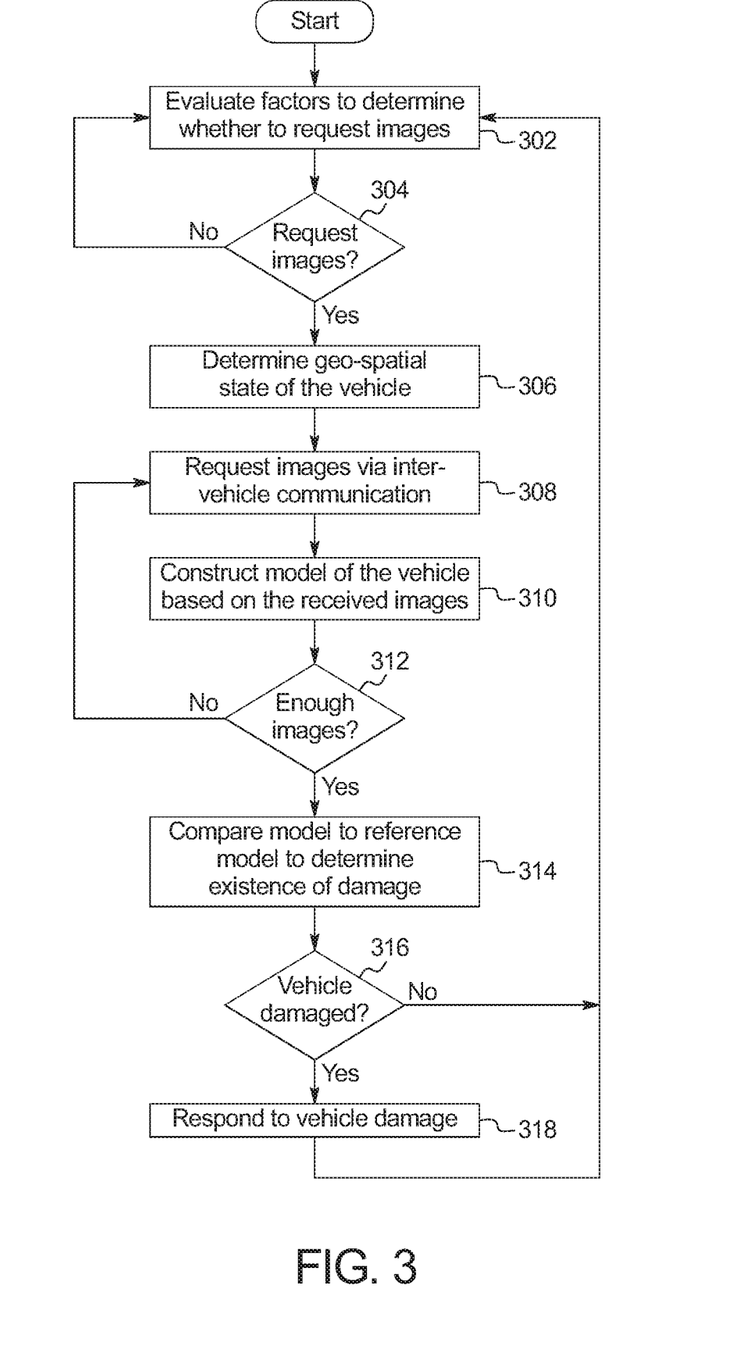
FIG. 3 is a flowchart of a method to use inter-vehicle communication and image analysis to detect exterior damage to the vehicle of FIG. 1, which may be implemented by the electronic components of FIG. 2.

FIG. 3 is a flowchart of a method to use inter-vehicle communication and image analysis to detect exterior damage to the vehicle 100 of FIG. 1, which may be implemented by the electronic components 200 of FIG. 2. Initially at block 302, the damage detector 116 monitors the area around the vehicle 100 and the characteristics of the vehicle 100 to detect trigger events. At block 304, the damage detector 116 determines whether a trigger event has occurred. For example, the damage detector 116 may determine that a trigger event occurred when (i) an object is detected close to the vehicle 100, (ii) a collision is detected, (iii) a person is detected lingering near the vehicle for a threshold period of time, (iv) a sound indicative of a collision is detected, (v) a threshold period of time has elapsed or a threshold distance has been traveled, (vi) the vehicle 100 is parked in an area with a threshold level of properly crime, (vii) inclement weather has been detected, and/or (viii) when the vehicle is parked for a threshold period of time, etc. When a trigger event has occurred, the method continues to block 306. Otherwise, when a triggering event has not occurred, the method returns to block 302.

At block 306, the damage detector 116 determines characteristics of the vehicle 100 to determine a geo-spatial orientation of the vehicle 100 that facilitates other vehicles 112 and/or roadside units 114 determining the relative location of the vehicle 100. At block 308, the damage detector 116 broadcasts a message via inter-vehicle communication requesting images. At block 310, the damage detector 116 constructs a composite model of the vehicle 100 based on the received images based on a structure from motion algorithm. At block 312, the damage detector 116 determines whether it has received enough images from the other vehicles 112 and/or the roadside unit 114 to perform the structure from motion. When enough images have been received, the method continues at block 314. Otherwise, when enough images have not been received, the method returns to block 308.

At block 314, the damage detector 116 compared the composite model generated at block 310 to the set of reference images stored in memory 206. At block 316, the damage detector 116 determines, based on the comparison, whether the vehicle 100 is damaged. When the vehicle 100 is damaged, the method continues at block 318. Otherwise, when the vehicle 100 is not damaged, the method returns to block 302.

The flowchart of FIG. 3 is representative of machine readable instructions stored in memory (such as the memory 206 of FIG. 2) that comprise one or more programs that, when executed by a processor (such as the processor 204 of FIG. 2), cause the vehicle 100 to implement the example damage detector 116 of FIGS. 1 and 2. Further, although the example program(s) is/are described with reference to the flowchart illustrated in FIG. 3, many other methods of implementing the example damage detector 116 may alternatively be used. For example, the order of execution of the blocks may be changed, and/or some of the blocks described may be changed, eliminated, or combined.

In this application, the use of the disjunctive is intended to include the conjunctive. The use of definite or indefinite articles is not intended to indicate cardinality. In particular, a reference to "the" object or "a" and "an" object is intended to denote also one of a possible plurality of such objects. Further, the conjunction "or" may be used to convey features that are simultaneously present instead of mutually exclusive alternatives. In other words, the conjunction "or" should be understood to include "and/or". As used here, the terms "module" and "unit" refer to hardware with circuitry to provide communication, control and/or monitoring capabilities, often in conjunction with sensors. "Modules" and "units" may also include firmware that executes on the circuitry. The terms "includes," "including," and "include" are inclusive and have the same scope as "comprises," "comprising," and "comprise" respectively.

The above-described embodiments, and particularly any "preferred" embodiments, are possible examples of implementations and merely set forth for a clear understanding of the principles of the invention. Many variations and modifications may be made to the above-described embodiment(s) without substantially departing from the spirit and principles of the techniques described herein. All modifications are intended to be included herein within the scope of this disclosure and protected by the following claims.

What is claimed is:

1. A vehicle comprising:
   an inter-vehicle communication module; and
   a body control module to:
      monitor an area around the vehicle and characteristics of the vehicle to detect a triggering event;
      in response to detecting the trigger event:
         in response to determining that the area around the vehicle is either dark or crowded, cause the vehicle to reposition itself before requesting the images; and
         broadcast a request for images;
      generate a composite image based on the images;
      compare the composite image to a reference image to identify damage on the vehicle;
      in response to identifying damage, take an action specified by an operator.

2. The vehicle of claim 1, wherein the trigger event is detecting an object close to the vehicle within a margin of error of range detections sensors of the vehicle.

3. The vehicle of claim 1, wherein the trigger event is detecting an object colliding with the vehicle.

4. The vehicle of claim 1, wherein the trigger event is detecting a person proximate the vehicle for a threshold period of time while the vehicle is stationary.

5. The vehicle of claim 1, wherein the trigger event is detecting a sound indicative of a collision.

6. The vehicle of claim 1, wherein the trigger event is when the vehicle is stationary for a threshold period of time.

7. The vehicle of claim 6, wherein the threshold period of time is based on a crime rate at a location of the vehicle.

8. The vehicle of claim 1, wherein the body control module is to generate the composite image using a structure from motion algorithm.

9. A method to detect damage of a vehicle comprising:
monitoring, with trigger sensors, an area around the vehicle and characteristics of the vehicle to detect a triggering event;
in response to detecting the trigger event:
determining whether the area around the vehicle is either dark or crowded;
in response to determining that the area around the vehicle is either dark or crowded, causing the vehicle to reposition itself before requesting an image; and
broadcasting, via an inter-vehicle communication module, a request for images;
generating, with a processor, a composite image based on the images;
comparing the composite image to a reference image to identify damage on the vehicle; and
in response to identifying damage, take an action specified by an operator.

10. The method of claim 9, wherein the trigger event is detecting an object close to the vehicle within a margin of error of range detections sensors of the vehicle.

11. The method of claim 9, wherein the trigger event is detecting an object colliding with the vehicle.

12. The method of claim 9, wherein the trigger event is detecting a person proximate the vehicle for a threshold period of time while the vehicle is stationary.

13. The method of claim 9, wherein the trigger event is detecting a sound indicative of a collision.

14. The method of claim 9, wherein the trigger event is when the vehicle is stationary for a threshold period of time.

15. The vehicle of claim 14, wherein the threshold period of time is based on a crime rate at a location of the vehicle.

16. The method of claim 9, wherein generating the composite image includes using a structure from motion algorithm.

* * * * *